United States Patent [19]

DeLuca et al.

[11] Patent Number: 4,841,038

[45] Date of Patent: Jun. 20, 1989

[54] METHOD FOR PREPARING COENZYME A ESTERS OF ALL-TRANS- AND 13-CIS RETINOIC ACIDS

[75] Inventors: Hector F. DeLuca, Madison, Wis.; Andrzej Kutner, Warsaw, Poland; Heinrich K. Schnoes, Madison, Wis.

[73] Assignee: Wisconsin Alumni Research Foundation, Madison, Wis.

[21] Appl. No.: 190,443

[22] Filed: May 5, 1988

Related U.S. Application Data

[62] Division of Ser. No. 869,791, Jun. 2, 1986, Pat. No. 4,757,140.

[51] Int. Cl.$^4$ ............................................. C07H 19/20
[52] U.S. Cl. ........................................ 536/27; 548/542
[58] Field of Search ........................... 536/27; 548/542

*Primary Examiner*—David B. Springer
*Attorney, Agent, or Firm*—Howard W. Bremer

[57] ABSTRACT

The invention relates to a new method for preparing all trans- and 13-cis retinoyl CoA.

1 Claim, No Drawings

METHOD FOR PREPARING COENZYME A ESTERS OF ALL-TRANS- AND 13-CIS RETINOIC ACIDS

This application is a division of U.S. Ser. No. 869,791, filed June 2, 1986, U.S. Pat. No. 4,757,140.

DESCRIPTION

Field of the Invention

The present invention relates to novel derivatives of all-trans- and 13-cis-retinoic acid.

Background of the Invention

In 1967, 13-cis-retinoic acid was identified in rat tissue extracts and it was postulated to be a natural metabolite of all-trans-retinoic acid.[1] The 3-cis-retinoic acid has been found to be at least as effective as all-trans-rectinoic acid in promoting vitamin A-dependent growth as well as in controlling epithelial cell differentiation. Recent work suggests that 13-cis-retinoic acid is not solely produced as an artifact of isolation but that all-trans-retinoic acid is isomerized in mammals to some extent to 13-cis-retinoic acid.[2] The utility of 13-cis-retinoic acid in treating dermatological conditions, its tumor inhibitory properties, and its reduced toxicity relative to all-trans-retinoic acid are known.

DISCLOSURE OF THE INVENTION

The derivative of the present invention can be represented by the following formula:

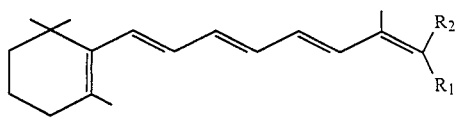

wherein $R_1$ and $R_2$ are each selected from the group consisting of:

(a) hydrogen,

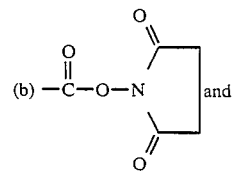 and

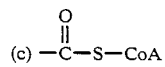

where CoA represents coenzyne A, except that both of $R_1$ and $R_2$ cannot be (a), but one of $R_1$ and $R_2$ must be (a).

The compounds of the present invention can be prepared in accordance with the following schematic diagram and description.

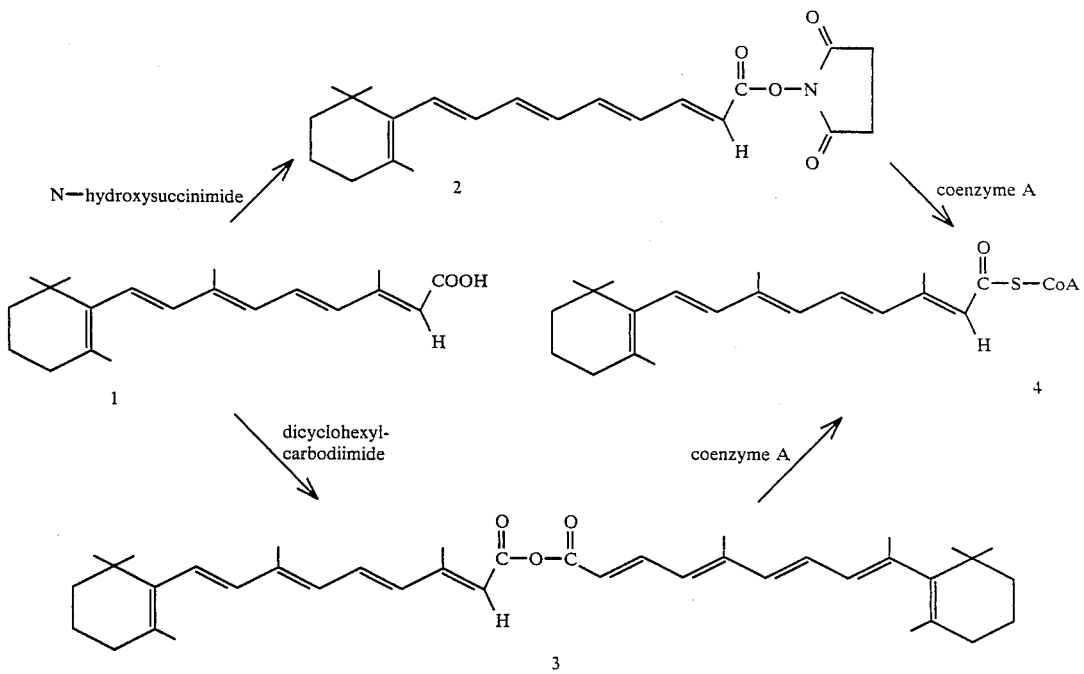

where
1 = all trans-retinoic acid
2 = N-hydroxysuccinimidyl all trans-retinoate
3 = all trans-retinoic acid anhydride
4 = all trans-retinoyl CoA The present invention relates to novel derivatives of all-trans- and 13-cis-retinoic acid. More specifically, this invention relates to N-hydroxysuccinimidyl and coenzyme A esters of all-trans- and 13-cis-retinoic acid.

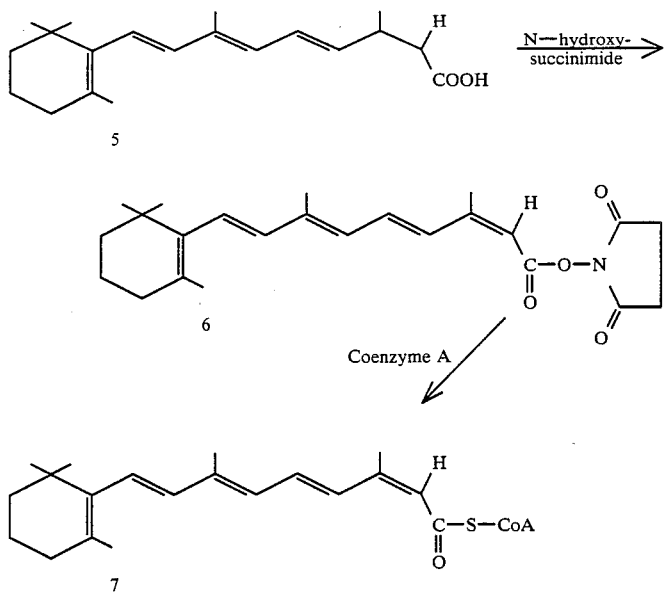

where
5 = 13-cis-retinoic acid
6 = N-hydroxysuccinimidyl 13-cis-retinoate
7 = 13-cis-retinoyl CoA

DETAILED DESCRIPTION OF PROCESSES

Chemicals

All trans-retinoic acid and the sodium salt of coenzyme A were purchased from Sigma Chemical Co. (St. Louis, MO). N-Hydroxysuccinimide and N,N'-dicyclohexylcarbodiimide were from the Aldrich Chemical Co. (Milwaukee, WI). Disposable silica gel Sep-Pak cartridges (Waters Associates, Milford, MA) were used for purification of synthetic intermediates.

All operations involving the use of retinoic acid analogs were performed under yellow light in a nitrogen atmosphere. Glassware silanized with dimethyldichlorosilane was used for the synthesis, handling and storage of retinoic acid CoA thioesters. All reactions were done using 1 and 5 ml Reacti-Vials (Pierce Chem. Corp., Rockford, IL).

Chromatographic Technique

Analytical and preparative thin-layer chromatography (TLC) was done using precoated aluminum silica gel sheets with UV indicator and glass pre-coated silica gel plates (20×20 cm, 2 mm thick) without fluorescence indicator, respectively, obtained from EM Science (Gibbstown, NJ). Plates were developed using solvent systems: A; hexane-ethyl acetate 1:1 and B; n-butanol-acetic acid-water 5:2:3.

Spectrometric Analyses

Electron impact mass spectra (EI-MS) were recorded at 70 eV with an AEI MS-9 spectrometer coupled to a DS-50 data system.

Ultraviolet (UV) absorption spectra were recorded in absolute ethanol or dioxane with a Hitachi Model 100-60 UV-visible spectrophotometer.

Infrared spectra (IR) were recorded on a Nicolet MX-1 FT-IR spectrometer in $CCl_4$ solution or using films of oily substances.

Proton magnetic resonance spectra ($^1$H-NMR) were taken with a Bruker WH-270 FT spectrometer in acetone-$d_6$ solutions containing tetramethylsilane (TMS) as internal standard.

Beckman model 4500 pH meter equipped with Beckman COMB pH-electrode was used for pH adjustments.

PREPARATIONS

Preparation of N-hydroxysuccinimidyl ester of all-trans-retinoic acid (2)

All-trans-retinoic acid (1) (20 mg, 64 μM) in 0.8 ml of dioxane was treated with N-hydroxysuccinimide (7.6 mg, 64 μM) in 0.4 ml of dioxane and dicyclohexylcarbodiimide (13.6 mg, 64 μM) in 0.4 ml of dioxane. The resulting solution was magnetically stirred at room temperature for 5 hours and then diluted with 10 ml of ethyl ether. The precipitated dicyclohexylurea was separated by filtration and the filtrate evaporated to dryness under reduced pressure. The oily residue was dissolved in warm methanol (10 ml) and the solution concentrated under reduced pressure until a slight precipitate became apparent. After standing overnight at −20° C, crystals were filtered off and washed with cold methanol. Chromatographically pure product (2) showed TLC $R_f$ 0.47 (solvent system A). UV (ethanol) $\lambda_{max}$ 377 (36.400); IR 1758, 1734 cm$^{-1}$; NMR (acetone-$d_6$) δ 1.05 (s, 6,($CH_3$)$_2$C), 1.5 (m, 2, 2—$CH_2$), 1.6 (m, 2, 3—$CH_2$), 1.72 (s, 3, 5—$CH_3$), 2.01 (s, 3, 9—$CH_3$), 2.02 (2, 4—$CH_2$), 2.37 (s, 3, 13—$CH_3$), 2.97 (s, 4, 1'—$CH_2$ 2'—1 $CH_2$); MS, m/e (relative intensity) (M)+397 (65), 382 (5), 299 (12), 283 (40), 267 (19), 255 (10), 239 (17), 69 (100).

Preparation of all-trans-retinoic acid anhydride (3)

All trans-retinoic acid (10 mg, 33 μM) in 0.2 ml of tetrahydrofuran was treated with dicyclohexylcarbodiimide (7.2 mg, 34 μM) in 0.2 ml of acetonitrile. The solution was stirred at room temperature for 2 hours and then diluted with ethyl ether. Precipitated dicyclohexylurea was removed by filtration and solvent evaporated under reduced pressure. The residue was suspended in hexane and chromatographed on a Sep- Pak cartridge. Anhydride 3 was eluted from the cartridge with the mixture of 1.5% propanol-2 in hexane (20 ml). Further elution with the same mixture afforded the unreacted substrate contaminated with the product of condensation of dicyclohexylcarbodiimide with all-trans-retinoic acid. The pure anhydride 3 (solvent system A) was obtained as an oily substance (from hexane). TLC, $R_f$ 0.81 (solvent system A). UV (ethanol) $\lambda_{max}$ 384 ($\epsilon$76,000) [$\lambda_{max}$ 385, $\epsilon$68,300 (ethanol)]; IR 1701, 1767 cm$^{-1}$; NMR (acetone-d$_6$) $\delta$1.04 (s, 12, (CH$_3$)$_2$C), 1.5 (m, 4, 2—CH$_2$), 1.6 (m, 4, 3—CH$_2$), 1.74 (6, s, 5—CH$_3$), 2.1 (m, 10, 4—CH$_2$, 9—CH$_3$), 2.44 (s, 6, 13—CH$_3$). MS, m/e (relative intensity) (M)$^+$582 (7), 444 (3.6), 404 (5.4), 381 (9.4), 366 (4.6), 243 (7), 177 (7), 159 (26), 145 (17), 44 (100).

Preparation of all-trans-retinoic acid CoA ester (4)

N-hydroxysuccinimidyl ester of all-trans-retinoic acid (2) (1.5 mg, 3.7 $\mu$M) in 0.4 ml of tetrahydrofuran was added to a stirred solution of coenzyme A (2.5 mg, 2.8 $\mu$m) in 0.2 ml of water. The pH of the solution was adjusted to 8.0–8.5 with 1% NaHCO$_3$. The reaction mixture was stirred under nitrogen atmosphere at 35° C. for 20 hours until most of the CoA was consumed as determined by TLC using the solvent system B. Ester 4 was separated from the crude reaction mixture by preparative TLC using the solvent system B. Product was extracted from the TLC adsorbent using a mixture of acetic acid and water. Lyophilization of the extract afforded pure ester 4 as determined by TLC using the solvent system B ($R_f$ 0.43, comparing with $R_f$ 0.40 and 0.41 for $\alpha$-methylcrotonyl and myristoyl esters of CoA). UV (H$_2$O) $\lambda_{max}$ 258 ($\epsilon$ 10,500 and $\lambda_{max}$ 393 ($\epsilon$ 32,000).

Ester 4 was also obtained starting from anhydride 3 using the same procedure and separation method as above. In this preparation, however, the formation of ester 4 could not be completed even when coenzyme A was exposed to a 2-3-fold molar excess of anhydride 3 for double the time in above preparation.

Preparation of N-hydroxysuccinimidyl ester of 13-cis-retinoic acid (6)

The compound 6 was prepared by the method essentially the same as for preparation of ester 2 starting from 13-cis-retinoic acid 5. TLC of chromatographically pure compound 6 showed $R_f$ 0.53 (solvent system A). UV (ethanol) $\lambda_{max}$ 380 ($\epsilon$ 35,000); IR 1760, 1747 cm$^{-1}$, NMR (acetone-d$_6$) $\delta$ 1.05 (s, 6, (CH$_3$)$_2$C), 1.5 (m, 2, 2—CH$_2$), 1.65 (m, 2, 3—CH$_2$), 1.76 (s, 3, 5—CH$_3$), 2.05 (m, 2, 4—CH$_2$), 2.1 (s, 3, 9—CH$_3$), 2.88 (s, 4, 1'—CH$_2$, 2'—CH$_2$); MS, m/e (relative intensity) (M)$^+$ 397 (36), 382 (2), 353 (7), 283 (17), 267 (10), 255 (8), 239 (19), 41 (100).

Preparation of 13-cis-retinoic acid CoA ester (7)

Ester 7 was prepared and purified by the method described for the preparation of ester 4. TLC of chromatographically pure product showed $R_f$ 0.42 in solvent system B.

The compounds of this invention find utility in the treatment of dermatological conditions such as acne and ichthyosis, and as substitutes for all-trans-retinoic acid and 13-cis-retinoic acid in their various known applications. They may also be used as a substrate for biochemical reactions, such as, the transfer of retinoic acid to glycerol derivatives or diglycerides or in the $\beta$ and omega oxidation of retinoic acid.

We claim:

1. A method for preparing all-trans and 13-cis-retinoyl CoA which comprises treating, respectively, all-trans or 13-cis-retinoic acid with N-hydroxysuccinimide, separating formed dicyclohexylurea from the reaction mixture, recovering the respective N-succinimidyl esters of all-trans or 13-cis-retinoic acid, reacting said respective esters with a solution of Coenzyme A and recovering all-trans-retinoyl CoA or 13-cis-retinoyl CoA.

* * * * *